United States Patent
Lockemeyer et al.

(10) Patent No.: US 8,937,031 B2
(45) Date of Patent: Jan. 20, 2015

(54) EPOXIDATION CATALYST, A PROCESS FOR PREPARING THE CATALYST, AND A PROCESS FOR THE PRODUCTION OF AN OLEFIN OXIDE

(75) Inventors: John Robert Lockemeyer, Sugar Land, TX (US); Marek Matusz, Houston, TX (US); Randall Clayton Yeates, Sugar Land, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/581,641

(22) PCT Filed: Feb. 24, 2011

(86) PCT No.: PCT/US2011/026039
§ 371 (c)(1),
(2), (4) Date: Aug. 29, 2012

(87) PCT Pub. No.: WO2011/109215
PCT Pub. Date: Sep. 9, 2011

(65) Prior Publication Data
US 2012/0323026 A1    Dec. 20, 2012

Related U.S. Application Data

(60) Provisional application No. 61/309,174, filed on Mar. 1, 2010.

(51) Int. Cl.
| | |
|---|---|
| *B01J 21/00* | (2006.01) |
| *B01J 23/00* | (2006.01) |
| *B01J 25/00* | (2006.01) |
| *B01J 29/00* | (2006.01) |
| *B01J 31/00* | (2006.01) |
| *B01J 27/047* | (2006.01) |
| *C07C 213/04* | (2006.01) |
| *B01J 27/051* | (2006.01) |
| *B01J 27/188* | (2006.01) |
| *B01J 27/19* | (2006.01) |
| *B01J 35/10* | (2006.01) |
| *B01J 37/02* | (2006.01) |
| *C07D 301/10* | (2006.01) |

(52) U.S. Cl.
CPC ............. *B01J 27/051* (2013.01); *C07C 213/04* (2013.01); *B01J 27/047* (2013.01); *B01J 27/188* (2013.01); *B01J 27/19* (2013.01); *B01J 35/108* (2013.01); *B01J 37/0201* (2013.01); *B01J 35/1095* (2013.01); *C07D 301/10* (2013.01)
USPC ........................... 502/219; 502/100; 502/150

(58) Field of Classification Search
USPC ........................ 502/219, 100, 150
See application file for complete search history.

(56) References Cited

U.S. PATENT DOCUMENTS

| | | | |
|---|---|---|---|
| 3,950,507 A | 4/1976 | Kuklina et al. | 423/626 |
| 4,242,235 A | 12/1980 | Cognion et al. | 252/455 |
| 4,379,134 A * | 4/1983 | Weber et al. | 423/626 |
| 4,740,493 A | 4/1988 | Boehning et al. | 502/348 |
| 4,761,394 A * | 8/1988 | Lauritzen | 502/348 |
| 4,766,105 A * | 8/1988 | Lauritzen | 502/216 |
| 4,822,900 A | 4/1989 | Hayden | 549/534 |
| 5,100,859 A | 3/1992 | Gerdes et al. | 502/439 |
| 5,145,824 A | 9/1992 | Buffum et al. | 502/216 |
| 5,380,697 A | 1/1995 | Matusz et al. | 502/348 |
| 5,384,302 A | 1/1995 | Gerdes et al. | 502/439 |
| 5,512,530 A | 4/1996 | Gerdes et al. | 502/351 |
| 5,733,842 A | 3/1998 | Gerdes et al. | 502/439 |
| 5,739,075 A | 4/1998 | Mautusz | 502/514 |
| 5,801,259 A | 9/1998 | Kowaleski | 549/536 |
| 6,040,467 A | 3/2000 | Papavassiliou et al. | 549/534 |
| 6,080,897 A | 6/2000 | Kawabe | 568/858 |
| 6,368,998 B1 | 4/2002 | Lockemeyer | 502/347 |
| 7,479,565 B2 | 1/2009 | Yeates et al. | 549/536 |
| 7,507,844 B2 * | 3/2009 | Pak | 549/534 |

(Continued)

FOREIGN PATENT DOCUMENTS

| | | | |
|---|---|---|---|
| EP | 3642 | 8/1979 | C07D 301/10 |
| WO | WO0015333 | 3/2000 | B01J 23/50 |

(Continued)

OTHER PUBLICATIONS

Brunauer, S. et al; "Adsorption of Gasses in Multimolecular Layers"; Journal of the American Chemical Society 60; pp. 309-316; Feb. 1938.

Wang, F.F.Y.; "Ceramic Fabrication Processes"; Treatise on Materials Science and Technology; vol. 9; pp. 71-93; 1976.

"Carbon and Graphite Fibers to Chlorocarbons and Chlorohydrocarbons-C"; Kirk-Othmer Encyclopedia of Chemical Technology, 4th ed., vol. 5; p. 610 ff.

(Continued)

*Primary Examiner* — James McDonough

(57) ABSTRACT

A catalyst for the epoxidation of an olefin comprising a carrier and, deposited thereon, silver, a rhenium promoter, a first co-promoter, and a second co-promoter; wherein
  the quantity of the rhenium promoter deposited on the carrier is greater than 1 mmole/kg, relative to the weight of the catalyst;
  the first co-promoter is selected from sulfur, phosphorus, boron, and mixtures thereof;
  the second co-promoter is selected from tungsten, molybdenum, chromium, and mixtures thereof;
  the total quantity of the first co-promoter and the second co-promoter deposited on the carrier is at most 5.0 mmole/kg, relative to the weight of the catalyst; and
  wherein the carrier has a monomodal, bimodal or multimodal pore size distribution, a pore diameter of 0.01-200 μm, a specific surface area of 0.03-10 m$^2$/g, a pore volume of 0.2-0.7 cm$^3$/g, wherein the median pore diameter is 0.1-100 μm, and a water absorption of 10-80%.

18 Claims, No Drawings

(56) References Cited

U.S. PATENT DOCUMENTS

| | | | |
|---|---|---|---|
| 7,507,845 B1 * | 3/2009 | Gueckel | 549/536 |
| 7,560,411 B2 | 7/2009 | Yeates et al. | 502/317 |
| 7,560,577 B2 | 7/2009 | Hirota et al. | 549/534 |
| 2003/0162984 A1 | 8/2003 | Lockemeyer et al. | 549/534 |
| 2008/0081920 A1 | 4/2008 | Gueckel | 549/533 |
| 2008/0306289 A1 | 12/2008 | Matusz et al. | 549/518 |
| 2009/0062556 A1 | 3/2009 | Pak | 549/534 |
| 2009/0131695 A1 | 5/2009 | Gerdes et al. | 549/534 |
| 2009/0177016 A1 * | 7/2009 | Lockemeyer et al. | 568/680 |
| 2009/0198076 A1 | 8/2009 | Guckel | 549/536 |
| 2009/0281118 A1 | 11/2009 | Bunnelle et al. | 514/255.05 |

FOREIGN PATENT DOCUMENTS

| | | |
|---|---|---|
| WO | 2007095453 | 8/2007 |
| WO | 2009137431 | 11/2009 |

OTHER PUBLICATIONS

Reed, J.S.; "Flocculants, Binders, and Bonds" Introduction to the Principles of Ceramic Processing; pp. 152-173; 1988.

European Patent Office Search Report dated Feb. 19, 2014 for Application No. 11751090.9, PCT US2011026039.

* cited by examiner

EPOXIDATION CATALYST, A PROCESS FOR PREPARING THE CATALYST, AND A PROCESS FOR THE PRODUCTION OF AN OLEFIN OXIDE

PRIORITY CLAIM

The present application claims priority from PCT/US2011/026039, filed 24 Feb. 2011, which claims priority from U.S. provisional 61/309,174, filed 1 Mar. 2010.

FIELD OF THE INVENTION

The present invention relates to an epoxidation catalyst, a process for preparing the catalyst, and a process for the production of an olefin oxide, a 1,2-diol, a 1,2-diol ether, a 1,2-carbonate, or an alkanolamine.

BACKGROUND OF THE INVENTION

In olefin epoxidation, a feed containing an olefin and oxygen is contacted with a catalyst under epoxidation conditions. The olefin is reacted with oxygen to form an olefin oxide. A product mix results that contains olefin oxide and, typically, unreacted feed and combustion products.

The olefin oxide may be reacted with water to form a 1,2-diol, with carbon dioxide to form a 1,2-carbonate, with an alcohol to form a 1,2-diol ether, or with an amine to form an alkanolamine. Thus, 1,2-diols, 1,2-carbonates, 1,2-diol ethers, and alkanolamines may be produced in a multi-step process initially comprising olefin epoxidation and then the conversion of the formed olefin oxide with water, carbon dioxide, an alcohol, or an amine.

Olefin epoxidation catalysts typically comprise a silver component, usually with one or more additional elements deposited therewith, on a carrier. U.S. Pat. No. 4,766,105 discloses an ethylene oxide catalyst comprising silver, alkali metal, rhenium and a rhenium co-promoter selected from sulfur, molybdenum, tungsten, chromium and mixtures thereof supported on a carrier. The ethylene oxide catalyst described in U.S. Pat. No. 4,766,105 provides an improvement in one or more catalytic properties.

The catalyst performance may be assessed on the basis of selectivity, activity and stability of operation. The selectivity is the fraction of the converted olefin yielding the desired olefin oxide. As the catalyst ages, the fraction of the olefin converted normally decreases with time and to maintain a constant level of olefin oxide production the temperature of the reaction may be increased.

The selectivity determines to a large extent the economical attractiveness of an epoxidation process. For example, one percent improvement in the selectivity of the epoxidation process can substantially reduce the yearly operating costs of a large scale ethylene oxide plant. Further, the longer the activity and selectivity can be maintained at acceptable values, the longer the catalyst charge can be kept in the reactor and the more product is obtained. Quite modest improvements in the selectivity, activity, and maintenance of the selectivity and activity (i.e., stability) over long periods yield substantial dividends in terms of process efficiency.

One means to affect the selectivity, activity and/or stability of an EO catalyst is to use a specific carrier having certain properties, such as a specific range of pore size distribution and/or surface area. The selection of the particular carrier will then result in various changes in selectivity or activity. Another means to affect the selectivity of an EO catalyst is to adjust the components of the catalyst put onto the carrier. The following patents/published patent applications relate to improved EO catalysts based on either differences in the carrier or changes to the catalyst components: U.S. Pat. Nos. 4,242,235; 4,740,493; 4,766,105; 7,507,844; 7,507,845; 7,560,577; 7,560,411; US 2009/0281118; US 2009/0062556; US 2008/0081920; US 2008/0306289; US 2009/0131695 and US 2009/0198076. Further improvements are needed, particularly to develop EO catalysts resulting in improved selectivity along with improved stability.

SUMMARY OF THE INVENTION

The present invention provides for a catalyst for the epoxidation of an olefin wherein the catalyst exhibits not only improved selectivity, but also improved stability. This improvement results from selecting a specific carrier for the specific catalyst composition, which carrier may be monomodal, bimodal or multimodal with regard to pore size distribution. In particular, the present invention provides a catalyst for the epoxidation of an olefin comprising a specific carrier and, deposited on the carrier, silver, a rhenium promoter, a first co-promoter, and a second co-promoter; wherein a) the quantity of the rhenium promoter deposited on the carrier is greater than 1 mmole/kg, relative to the weight of the catalyst;

b) the first co-promoter is selected from sulfur, phosphorus, boron, and mixtures thereof;

c) the second co-promoter is selected from tungsten, molybdenum, chromium, and mixtures thereof;

d) the total quantity of the first co-promoter and the second co-promoter deposited on the carrier is at most 5.0 mmole/kg, relative to the weight of the catalyst; and e) the carrier is predominately α-alumina having a monomodal, bimodal or multimodal pore size distribution with a pore diameter range of 0.01-200 μm, a specific surface area of 0.03-10 m²/g, a pore volume of 0.2-0.7 cm³/g, wherein the median pore diameter of said carrier is 0.1-100 μm and has a water absorption of 10-80%.

The invention also provides a process for preparing an epoxidation catalyst comprising depositing silver, a rhenium promoter, a first co-promoter, and a second co-promoter on a specific carrier wherein:

a) the quantity of the rhenium promoter deposited on the carrier is greater than 1 mmole/kg, relative to the weight of the catalyst;

b) the first co-promoter is selected from sulfur, phosphorus, boron, and mixtures thereof;

c) the second co-promoter is selected from tungsten, molybdenum, chromium, and mixtures thereof;

d) the total quantity of the first co-promoter and the second co-promoter deposited on the carrier is at most 5.0 mmole/kg, relative to the weight of the catalyst; and e) the carrier is predominately α-alumina having a monomodal, bimodal or multimodal pore size distribution with a pore diameter range of 0.01-200 μm, a specific surface area of 0.03-10 m²/g, a pore volume of 0.2-0.7 cm³/g, wherein the median pore diameter of said carrier is 0.1-100 μm and has a water absorption of 10-80%.

The invention also provides a process for the epoxidation of an olefin comprising reacting the olefin with oxygen in the presence of an epoxidation catalyst prepared according to this invention.

Further, the invention provides a method of preparing a 1,2-diol, a 1,2-diol ether, a 1,2-carbonate, or an alkanolamine comprising obtaining an olefin oxide by the process for the epoxidation of an olefin according to this invention, and converting the olefin oxide into the 1,2-diol, the 1,2-diol ether, the 1,2-carbonate, or the alkanolamine.

DETAILED DESCRIPTION OF THE INVENTION

A highly selective epoxidation catalyst comprising a rhenium promoter in a quantity of more than 1 mmole/kg of the catalyst and a catalytically effective amount of silver as well as a first co-promoter and a second co-promoter in a total quantity of at most 5.0 mmole/kg catalyst, in accordance with the invention, exhibits an unexpected improvement in catalytic performance, in particular an improvement in initial selectivity, compared to a like catalyst not in accordance with the invention. Further, the catalyst is made with a specific carrier (which carrier may be characterized as monomodal, bimodal or multimodal) chosen in order to maximize catalyst performance.

Carrier Properties

"Surface area" as used herein is understood to refer to the surface area as determined by the nitrogen BET (Brunauer, Emmett and Teller) method as described in Journal of the American Chemical Society 60 (1938) pp. 309-316. The carriers of the present invention have a surface area of 0.03-10 $m^2/g$.

As used herein, water absorption is deemed to have been measured in accordance with ASTM C393, and water absorption is expressed as the weight of the water that can be absorbed into the pores of the carrier, relative to the weight of the carrier. The carriers of the present invention have water absorption of 10 to 80%.

The pore size distribution may be measured by a conventional mercury intrusion porosimetry device in which liquid mercury is forced into the pores of a carrier. Greater pressure is needed to force the mercury into the smaller pores and the measurement of pressure increments corresponds to volume increments in the pores penetrated and hence to the size of the pores in the incremental volume. As used herein, the pore size distribution, the median pore diameters and the pore volumes are as measured by mercury intrusion porosimetry to a pressure of $2.1 \times 10^8$ Pa using a Micromeretics Autopore 9200 model (130° contact angle, mercury with a surface tension of 0.480 N/m, and correction for mercury compression applied). As used herein, the median pore diameter is the pore diameter at which half of the total pore volume is contained in pores having a larger pore diameter and half of the total pore volume is contained in pores having a smaller pore diameter. The carriers of the present invention have a pore diameter range of 0.01-200 μm wherein the median pore diameter of the carrier is 0.1-100 μm.

The median particle size, referred to herein as "$d_{50}$", is as measured by a Horiba LA900 particle size analyzer and represents a particle diameter at which there are equal spherical equivalent volumes of particles larger and particles smaller than the stated median particle size. The method includes dispersing the particles by ultrasonic treatment, thus breaking up secondary particles into primary particles. This sonification treatment is continued until no further change in the $d_{50}$ value is noticed, which typically requires a 5 minute sonification when using the Horiba LA900 particle size analyzer.

As used herein, pore volume (ml/g), surface area ($m^2/g$) and water absorption (g/g) are defined relative to the weight of the carrier, unless stated otherwise.

Examples of Various Carriers

Carriers Described in US 2009/0062556

One example of a monomodal carrier is found in US Published Patent Application 2009/0062556, which disclosure is herein incorporated by reference. In the '556 application the carrier has no or little absolute volume from small pores, of less than 1 micrometer, and large pores, of above 5 micrometer. By "no or little absolute volume from small pores of less than 1 micron" it is meant that the pore volume of such pores is less than 0.20 ml/g. By "no or little absolute volume from large pores of above 5 micron" it is meant that the pore volume of such pores is less than 0.20 ml/g. In general terms, this carrier has a pore volume from pores with less than 1 micron in diameter of less than 0.20 ml/g and a pore volume from pores with greater than 5 micron in diameter of less than 0.20 ml/g. In particular, the inventive carrier has a total pore volume from 0.2 ml/g to 0.7 ml/g, a surface area from about 0.3 to about 3.0 $m^2/g$, at least 40% of pore volume from pores with diameters between 1 and 5 micrometers, and a median pore diameter between 1 and 5 micrometers, and wherein the pore volume from pores with a diameter of greater than 5 micrometers is less than 0.20 ml/g and the pore volume from pores with a diameter of less than 1 micrometer is less than 0.20 ml/g.

Carriers Described in US 2009/0177016

One useful carrier for use in this invention is disclosed in US Published Patent Application 2009/0177016, which disclosure is herein incorporated by reference. The carrier disclosed therein has a surface area of at least 1 $m^2/g$, and a pore size distribution such that pores with diameters in the range of from 0.2 to 10 μm represent at least 70% of the total pore volume and such pores together provide a pore volume of at least 0.27 ml/g, relative to the weight of the carrier. The process for the preparation of the carrier comprises forming a mixture comprising: a) from 50 to 90% w of a first particulate α-alumina having an average particle size ($d_{50}$) of from more than 10 up to 100 μm; and b) from 10 to 50% w of a second particulate α-alumina having an average particle size ($d_{50}$) of from 1 to 10 μm; % w being based on the total weight of α-alumina in the mixture; and shaping the mixture into formed bodies and firing the formed bodies to form the carrier.

Carriers Described in US 2009/0131695

In accordance with this invention, another useful carrier has a pore size distribution such that at least 80% of the total pore volume is contained in pores with diameters in the range of from 0.1 to 10 μm, and at least 80% of the pore volume contained in the pores with diameters in the range of from 0.1 to 10 μm is contained in pores with diameters in the range of from 0.3 to 10 μm. Such a carrier is disclosed in US Published Patent Application 2009/0131695, which disclosure is herein incorporated by reference. Preferably, the pore size distribution is such that the pores with diameters in the range of from 0.1 to 10 μm represent at least 85%, in particular at least 90% of the total pore volume. Typically, the pore size distribution is such that pores with diameters less than 0.1 μm represent less than 10%, more typically at most 5% of the total pore volume. The invention contemplates pores with diameters less than 0.1 μm approaching, if not reaching, zero percent of the total pore volume.

The carriers may have a median pore diameter of more than 0.5 μm. Typically, the median pore diameter is at most 2.1 μm.

Carriers Described in U.S. Pat. No. 7,507,577

Many examples of a bimodal or multimodal pore size distribution can be found in U.S. Pat. No. 7,507,577, which disclosure is herein incorporated by reference. In the '577 patent the pore size distribution of a carrier to be used for the catalyst has at least two peaks that are present in the range of pore diameter of 0.01-100 μm. At least one peak of the above at least two peaks is present in the range of pore diameter of 0.01-1.0 μm, preferably 0.04-0.8 μm, more preferably 0.1-0.5 μm and particularly preferably 0.2-0.4 μm. Preferably, at least one peak present in the range of 0.01-1.0 μm makes it easy to support a catalyst component in a fine and highly-dispersed state.

The size of the pore of a carrier is not particularly limited, but the median pore diameter is preferably 0.1-10 μm, more preferably 0.2-4.0 μm, still more preferably 0.3-3.0 μm and particularly preferably 0.4-1.5 μm. According to the patentee in the '577 patent, the median pore diameter of 0.1 μm or larger can repress sequential oxidation of ethylene oxide caused by retention of the product gas during the production of ethylene oxide. On the other hand, the median pore diameter of 10 μm or smaller can give practical strength to the carrier.

Carriers Described in U.S. Pat. No. 7,507,845; 2008/0081920; 2009/0198076

U.S. Pat. No. 7,507,845 and US Published Patent Applications 2008/0081920 also disclose a bimodal carrier, which disclosures are herein incorporated by reference. In these the solid support has a first mode of pores which have a mean diameter ranging from about 0.01 μm to about 5 μm. Preferably the first mode of pores has a mean diameter ranging from about 0.1 μm to about 4 μm. The support then has a second mode of pores, different from the first mode of pores, which second mode of pores has a mean diameter ranging from about 5 μm to about 30 μm. Preferably the second mode of pores has a mean diameter ranging from about 5 μm to about 20 μm. Usually, the first mode of pores comprises from about at most about 50% of the total pore volume and the second mode provides at least about 50% of the total pore volume. In another embodiment, the first mode of pores comprises at most about 45% of the total pore volume and the second mode provides at least about 55% of the total pore volume. In another embodiment, the first mode of pores comprises at most about 40% of the total pore volume and the second mode provides at least about 60% of the total pore volume. US Published Application 2009/0198076 is a related application and discusses carriers having at least two modes of pores, which disclosure is herein incorporated by reference.

Other Descriptions of Carriers

Further examples of monomodal, bimodal and multimodal carriers useful for EO catalysts according to the present invention can be found in U.S. Pat. Nos. 4,242,235, 4,740,493 and 4,766,105, which disclosures are herein incorporated by reference. One skilled in the art will understand that the limitations expressed herein may be optimized to obtain improved results.

Other Carrier Properties

In certain embodiments of this invention, the carrier exhibits a non-platelet morphology. As used herein, the term "non-platelet morphology" refers to the morphology of the carrier when imaged by scanning electron microscopy at a magnification of 2000, and to the substantial absence in such images of structures having substantially flat surfaces. By "substantial absence" of such structures it is meant that at most 25% of the structures have a substantially flat surface. By "substantially flat" it is meant that the radius of the curvature of the surface is at least 2 times the length of the largest dimension of the surface. The structures having a substantially flat surface have typically an aspect ratio of at most 4:1, the aspect ratio of a structure being the ratio of the largest dimension to the smallest dimension of the structure. The term "structures" refers to structural entities in the carrier which can be designated to represent individual particles of carrier material fused or bonded together to form the carrier.

The carrier may be based on a wide range of materials. Such materials may be natural or artificial inorganic materials and they may include refractory materials, silicon carbide, clays, zeolites, charcoal and alkaline earth metal carbonates, for example calcium carbonate. Preferred are refractory materials, such as alumina, magnesia, zirconia and silica. The most preferred material is α-alumina. Typically, the carrier comprises at least 85 weight percent, more typically at least 90 weight percent α-alumina.

Carriers may generally be made by firing particulate components at an elevated temperature until the particles sinter together. In general, firing may be continued until the particles are bonded together, either by the formation of bond posts from any added bond material or through sintering, but preferably not beyond the point at which the water absorption of the carrier is reduced.

Burnout materials may or may not be used in the firing process. Burnout materials are well known in the art (cf., for example, F F Y Wang (Ed.), "Treatise on Materials Science and Technology", Volume 9, (New York, 1976), pp. 79-81; or J S Reed, "Introduction to the Principles of Ceramic Processing", (New York, 1988), pp. 152 ff.). The burnout materials may be used to enhance preservation of the structure during a green, i.e. unfired, phase of the carrier preparation, for example the phase in which formed bodies are shaped, for example by extrusion. The burnout materials are removed during the firing. The use of burnout materials also allows more complete sintering without too great a reduction in water absorption of the carrier. The burnout materials are typically finely divided solid organic materials that volatilize or burn, leaving as little residue as possible.

It is also a common expedient to use a bond material, i.e. a material which reduces the length of sintering time applied to bond the particles together. The bond material may also form a coating on at least a part of the carrier surface, which makes the carrier surface more receptive. The bond material may be based on a silica-containing composition comprising a crystallization inhibitor, inhibiting the formation of crystalline silica-containing compositions.

The silica-containing compositions for use as a bond material may comprise an alkali metal silicate bond material, or preferably an alkaline earth metal silicate bond material. The bond material may further comprise a hydrated alumina and optionally a titanium component and/or a zirconium component.

It has been found that, suitably, alumina carriers for use in this invention may be made by a method which comprises forming a mixture of different particulate α-alumina and optionally in addition an alkaline earth metal silicate bond material; and then shaping the mixture into formed bodies and firing the formed bodies, typically at a temperature of from 1200 to 1550° C., to form the carrier.

The alumina particles are readily commercially available, or they may readily be made, for example, by subjecting more coarse materials to grinding and sieving operations. In an embodiment, the smaller particles may be prepared from the larger particles by grinding, and the ground and un-ground particles are then combined. In another embodiment, the desired mixture of large and small particles may be formed by grinding relatively large particles to the extent that the mixture of particles has the desired bimodal particle size distribution.

The alkaline earth metal silicate bond material may comprise an alkaline earth metal silicate, for example calcium silicate or, preferably, magnesium silicate. The alkaline earth metal silicate can also be in the form of natural materials such as talc, serpentine, pyroxene, amphibole, and olivine. Alternatively to or in addition to the alkaline earth metal silicate, the alkaline earth metal silicate bond material may comprise a combination of an alkaline earth metal compound and a silica compound. Suitable alkaline earth metal compounds are alkaline earth metal salts, for example nitrates or sulfates, in particular magnesium nitrate or magnesium sulfate. Suitable silica compounds are silica sol, precipitated silica, amorphous silica, amorphous alkali metal silica, or amorphous alkali metal aluminosilicate. Amorphous silica compounds are preferred. The quantity of alkaline earth metal silicate bond material may suitably be in the range of from 0.2 to 10 weight percent, calculated as the total weight of alkaline earth metal oxide and silicate, as $SiO_2$, relative to the total weight of α-alumina in the mixture.

The alkaline earth metal silicate bond material may or may not comprise, as an additional component, a hydrated alumina. A suitable hydrated alumina is, for example, gibbsite, bayerite or diaspore. A preferred hydrated alumina is boehmite. The quantity of the hydrated alumina may suitably be in the range of from 0.1 to 15 weight percent, preferably from 0.2 to 10 weight percent, calculated as the weight of aluminium oxide, $Al_2O_3$, relative to the total weight of α-alumina in the mixture.

The alkaline earth metal silicate bond material may or may not comprise, as an additional component, a zirconium component, as a solid component or as a liquid component. Suitable zirconium components are zirconium dioxide and zirconium compounds which convert to zirconium dioxide upon firing. Such zirconium compounds may be salts, such as zirconyl nitrate, zirconyl sulfate or basic zirconyl carbonate. The quantity of the zirconium component may suitably be in the range of from 0 to 10 weight percent, more suitably from 0.2 to 5 weight percent, calculated as the weight of zirconium dioxide, $ZrO_2$, relative to the total weight of α-alumina in the mixture.

The alkaline earth metal silicate bond material may or may not comprise, as an additional component, a titanium component. Suitable titanium components are titanium dioxide, titanyl sulfate, titanyl oxalate, titanyl chloride, organo titanates, and other compounds which convert to titanium dioxide upon firing. Hydrated aluminas may in some instances be contaminated with titanium compounds and act as a source of the titanium component. The quantity of the titanium component may suitably be in the range of from 0 to 5 weight percent, more suitably from 0 to 1 weight percent, calculated as the weight of titanium dioxide, $TiO_2$, relative to the total weight of α-alumina in the mixture.

In a preferred embodiment, the carrier also contains a fluoride-containing species and a strength-enhancing additive into a carrier as described in U.S. Pat. No. 7,560,411, which disclosure is incorporated herein by reference. Fluoride-mineralized carriers are obtained by the incorporation of fluorine into the carrier. For purposes of the present invention, fluoride-mineralized carriers are obtained by combining alpha-alumina or alpha-alumina precursor(s) with a fluorine-containing species that is capable of liberating fluoride, typically as hydrogen fluoride, when the combination is calcined, and calcining the combination. Prior to calcining, the combination may be formed into formed bodies, for example by extrusion or spraying. Preferably, calcination is conducted at less than about 1,200° C., more preferably at less than about 1,100° C. Preferably, calcination is conducted at greater than about 900° C., more preferably at greater than about 1,000° C. If the temperature is sufficiently in excess of 1,200° C., the amount of fluoride liberated may be excessive and the morphology of the carrier may be detrimentally affected. The manner by which the fluoride-containing species is introduced into the carrier is not limited, and those methods known in the art for incorporating a fluorine-containing species into a carrier, and those fluoride-mineralized carriers obtained therefrom, may be used for the present invention. For example, U.S. Pat. Nos. 3,950,507 and 4,379,134 disclose methods for preparing fluoride-mineralized carriers and are hereby incorporated by reference. Typically, the amount of fluorine-containing species added to the carrier is at least about 0.1 percent by weight and typically no greater than about 5 percent by weight, calculated as the weight of elemental fluorine used relative to the weight of the carrier material to which the fluorine-containing species is being incorporated. Frequently, the fluorine-containing species is used in an amount from about 0.2 to about 3 percent by weight. More frequently, the fluorine-containing species is used in an amount from about 0.25 to about 2.5 percent by weight. These amounts refer to the amount of the species as initially added and do not necessarily reflect the amount that may ultimately be present in the finished carrier.

An advantage of the present invention is that the fluoride-mineralized carriers, or carriers having a particulate matrix having a lamellar or platelet-type morphology, have incorporated therein an additive that serves to increase the crush strength or attrition resistance of the carrier. Strength-enhancing additives are those species that when incorporated into the carrier result in an increase in the crush strength or improvement in the attrition resistance of the carrier. Suitably, the strength-enhancing additives are easily incorporated into the alumina crystal structure of the carrier, for example into the alumina crystal structure of a fluoride-mineralized carrier, by calcination at temperatures less than about 1,200° C., more preferably at less than about 1,100° C. Preferably, the strength-enhancing additive is capable of forming fluoride species, typically having a relatively low volatility so as to enhance their interaction with the carrier leading to the strength-enhancing effect. Strength-enhancing additives may be selected from the group consisting of a zirconium species, a lanthanide Group species, a Group II metal species, an inorganic glass, and mixtures thereof.

In an embodiment, the alkali metal silicate bond material may comprise an alkali metal silicate, for example amorphous sodium or lithium silicate.

Burnout materials may be selected from the group of polypropylenes, polyethylenes, carbohydrates, gums, flours, proteins, lignins, resins, waxes, alcohols, and esters. When preparing an α-alumina carrier, the quantity of burnout material may suitably be in the range of from 0.2 to 10 weight percent, more suitably from 0.5 to 5 weight percent, relative to the total weight of α-alumina in the mixture. The selection of the burnout material is considered not to be of any criticality to the invention. Also, in the practice of this invention using an α-alumina carrier, no burnout material may be used in the preparation of the carrier.

It is also preferred that the carrier particles be prepared in the form of formed bodies, the size of which is in general determined by the dimensions of an epoxidation reactor in which they are to be deposited. Generally however it is found very convenient to use particles such as formed bodies in the form of powder, trapezoidal bodies, cylinders, saddles, spheres, doughnuts, and the like. The cylinders may be solid or hollow, straight or bent, and they may have their length and cross-sectional dimensions about the same and from 5 to 10 mm.

The formed bodies can be formed from the mixture by any convenient forming process, such as spraying, spray drying, agglomeration or pressing, but preferably they are formed by extrusion of the mixture. For applicable methods, reference may be made to, for example, U.S. Pat. Nos. 5,145,824, 5,512,530, 5,384,302, 5,100,859 and 5,733,842, which are herein incorporated by reference. To facilitate such molding processes, in particular extrusion, the mixture may suitably be compounded with up to about 30 weight percent and preferably from 2 to 25 weight percent, based on the weight of the mixture, of extrusion aids and/or organic binders. Extrusion aids (also referred to by the term "processing aids") and organic binders are known in the art (cf., for example, "Kirk-Othmer Encyclopedia of Chemical Technology", 4$^{th}$ edition, Volume 5, pp. 610 ff.). Suitable examples may be petroleum jelly, hydrogenated oil, synthetic alcohol, synthetic ester, glycol, starch, polyolefin oxide or polyethylene glycol. Boric acid may also be added to the mixture, for example in a quantity of up to 0.5 weight percent, more typically in a quantity of from 0.01 to 0.5 weight percent, based on the weight of the mixture. The effect of the presence of boric acid may be a reduced content of leachable alkali metal ions in the carrier after firing. Enough water may be added to the mixture to make the mixture extrudable (by the term "the weight of the mixture", as used hereinbefore, is meant the weight of the total mixture, but excluding the weight of any added water).

The formed bodies may be dried and fired at a temperature high enough to ensure that the alumina particles are joined together by a sintering action and/or by the formation of bond posts formed from the bond material, if incorporated in the mixture. Generally, drying may take place between 20 and 400° C. and preferably between 30 and 300° C., typically for a period of up to 100 hours and preferably from 5 minutes to 50 hours. Typically, drying is performed to the extent that the mixture contains less than 2 weight percent of water. Generally, firing may take place at a temperature of at least 1200° C., preferably between 1250 and 1550° C., typically for a period of up to about 8 hours and preferably from 2 to 6 hours. Drying and firing may be carried out in any atmosphere, such as in air, nitrogen, or helium, or mixtures thereof. Preferably, in particular when the formed bodies contain organic material, the firing is at least in part or entirely carried out in an oxidizing atmosphere, such as in an oxygen-containing atmosphere.

The performance of the catalyst may be enhanced if the carrier is washed, to remove soluble residues, before deposition of other catalyst ingredients on the carrier. On the other hand, unwashed carriers may also be used successfully. A useful method for washing the carrier comprises washing the carrier in a continuous fashion with hot, demineralised water, until the electrical conductivity of the effluent water does not further decrease. A suitable temperature of the demineralised water is in the range of 80 to 100° C., for example 90° C. or 95° C. Reference may be made to WO-00/15333 and U.S. Pat. No. 6,368,998, which are incorporated herein by reference.

Preparation of Silver Catalyst

The preparation of the silver catalyst is known in the art and the known methods are applicable to the preparation of the catalyst which may be used in the practice of this invention. Methods of depositing silver on the carrier include impregnating the carrier or carrier bodies with a silver compound containing cationic silver and/or complexed silver and performing a reduction to form metallic silver particles. For further description of such methods, reference may be made to U.S. Pat. Nos. 5,380,697, 5,739,075, 4,766,105, and 6,368, 998, which are incorporated herein by reference. Suitably, silver dispersions, for example silver sols, may be used to deposit silver on the carrier.

The reduction of cationic silver to metallic silver may be accomplished during a step in which the catalyst is dried, so that the reduction as such does not require a separate process step. This may be the case if the silver containing impregnation solution comprises a reducing agent, for example, an oxalate, a lactate or formaldehyde.

Appreciable catalytic activity is obtained by employing a silver content of the catalyst of at least 10 g/kg, relative to the weight of the catalyst. Preferably, the catalyst comprises silver in a quantity of from 10 to 500 g/kg, more preferably from 50 to 450 g/kg, for example 105 g/kg, or 120 g/kg, or 190 g/kg, or 250 g/kg, or 350 g/kg. As used herein, unless otherwise specified, the weight of the catalyst is deemed to be the total weight of the catalyst including the weight of the carrier and catalytic components, for example silver, rhenium promoter, first and second co-promoters and further elements, if any.

The catalyst for use in this invention additionally comprises a rhenium promoter component deposited on the carrier in a quantity of greater than 1 mmole/kg, relative to the weight of the catalyst. Preferably, the rhenium promoter may be present in a quantity of at least 1.25 mmole/kg, more preferably at least 1.5 mmole/kg, most preferably at least 2 mmole/kg of the catalyst. Preferably, the rhenium promoter may be present in a quantity of at most 500 mmole/kg, more preferably at most 50 mmole/kg, most preferably at most 10 mmole/kg, relative to the weight of the catalyst. Preferably, the rhenium promoter may be present in a quantity in the range of from 1.25 to 50 mmole/kg, more preferably from 1.75 to 25 mmole/kg, most preferably from 2 to 10 mmole/kg, relative to the weight of the catalyst. The form in which the rhenium promoter may be deposited onto the carrier is not material to the invention. For example, the rhenium promoter may suitably be provided as an oxide or as an oxyanion, for example, as a rhenate or perrhenate, in salt or acid form.

The catalyst for use in this invention additionally comprises a first co-promoter component. The first co-promoter may be selected from sulfur, phosphorus, boron, and mixtures thereof. It is particularly preferred that the first co-promoter comprises, as an element, sulfur.

The catalyst for use in this invention additionally comprises a second co-promoter component. The second co-promoter component may be selected from tungsten, molybdenum, chromium, and mixtures thereof. It is particularly preferred that the second co-promoter component comprises, as an element, tungsten and/or molybdenum, in particular tungsten. The form in which first co-promoter and second co-promoter components may be deposited onto the carrier is not material to the invention. For example, the first co-promoter and second co-promoter components may suitably be provided as an oxide or as an oxyanion, for example, as a tungstate, molybdate, or sulfate, in salt or acid form.

The total quantity of the first co-promoter and the second co-promoter deposited on the carrier is at most 5.0 mmole/kg, calculated as the total quantity of the elements (i.e., the total of sulfur, phosphorous, boron, tungsten, molybdenum and/or chromium) relative to the weight of the catalyst. Preferably, the total quantity of the first co-promoter and the second co-promoter may be at most 4.0 mmole/kg, more preferably at most 3 mmole/kg of catalyst. Preferably, the total quantity of the first co-promoter and the second co-promoter may be at least 0.1 mmole/kg, more preferably at least 0.5 mmole/kg, most preferably at least 1 mmole/kg of the catalyst.

In an embodiment, the molar ratio of the first co-promoter to the second co-promoter may be greater than 1. In this embodiment, the molar ratio of the first co-promoter to the second co-promoter may preferably be at least 1.25, more preferably at least 1.5, most preferably at least 2, in particular at least 2.5. The molar ratio of the first co-promoter to the second co-promoter may be at most 20, preferably at most 15, more preferably at most 10.

In an embodiment, the molar ratio of the rhenium promoter to the second co-promoter may be greater than 1. In this embodiment, the molar ratio of the rhenium promoter to the second co-promoter may preferably be at least 1.25, more preferably at least 1.5. The molar ratio of the rhenium promoter to the second co-promoter may be at most 20, preferably at most 15, more preferably at most 10.

The catalyst may preferably also comprise a further element deposited on the carrier. Eligible further elements may be selected from nitrogen, fluorine, alkali metals, alkaline earth metals, titanium, hafnium, zirconium, vanadium, thallium, thorium, tantalum, niobium, gallium, germanium, and mixtures thereof. Preferably, the alkali metals are selected from lithium, potassium, rubidium and cesium. Most preferably, the alkali metal is lithium, potassium and/or cesium. Preferably, the alkaline earth metals are selected from calcium, magnesium and barium. Preferably, the further element may be present in the catalyst in a total quantity of from 0.01 to 500 mmole/kg, more preferably from 0.05 to 100 mmole/kg, the total quantity of the element relative to the weight of the catalyst. The further element may be provided in any form. For example, salts or hydroxides of an alkali metal or an alkaline earth metal are suitable. For example, lithium compounds may be lithium hydroxide or lithium nitrate.

It is important to select a target value for potassium for the entire catalyst composition (carrier plus added catalyst components). For example if the target water extractable quantity of potassium is 10 mmole/g, relative to the weight of the catalyst, such target potassium level is achieved by measuring the potassium level of the carrier and adding sufficient additional potassium during the catalyst impregnation to achieve the target potassium level. A similar process for adding sodium could be applied in order to achieve the proper target level. Lithium and cesium could be treated the same way, except that they don't typically contain these impurities in the carrier. If they did, one could use the same procedure for the target.

The quantity of water extractable potassium in the catalyst is deemed to be the quantity insofar as it can be extracted from the catalyst. The extraction involves extracting a 2-gram sample of the catalyst three times by heating it in 25-gram portions of de-ionized water for 5 minutes at 100° C. and determining in the combined extracts the amount of potassium by using a known method, for example atomic absorption spectroscopy.

As used herein, unless otherwise specified, the quantity of alkali metal present in the catalyst and the quantity of water leachable components present in the carrier are deemed to be the quantity insofar as it can be extracted from the catalyst or carrier with de-ionized water at 100° C. The extraction method involves extracting a 10-gram sample of the catalyst or carrier three times by heating it in 20 ml portions of de-ionized water for 5 minutes at 100° C. and determining in the combined extracts the relevant metals by using a known method, for example atomic absorption spectroscopy.

As used herein, unless otherwise specified, the quantity of alkaline earth metal present in the catalyst and the quantity of acid leachable components present in the carrier are deemed to be the quantity insofar as it can be extracted from the catalyst or carrier with 10% w nitric acid in de-ionized water at 100° C. The extraction method involves extracting a 10-gram sample of the catalyst or carrier by boiling it with a 100 ml portion of 10% w nitric acid for 30 minutes (1 atm., i.e. 101.3 kPa) and determining in the combined extracts the relevant metals by using a known method, for example atomic absorption spectroscopy. Reference is made to U.S. Pat. No. 5,801,259, which is incorporated herein by reference.

Epoxidation Process

Although the present epoxidation process may be carried out in many ways, it is preferred to carry it out as a gas phase process, i.e. a process in which the feed is contacted in the gas phase with the catalyst which is present as a solid material, typically in a packed bed. Generally the process is carried out as a continuous process.

The olefin for use in the present epoxidation process may be any olefin, such as an aromatic olefin, for example styrene, or a di-olefin, whether conjugated or not, for example 1,9-decadiene or 1,3-butadiene. Typically, the olefin is a monoolefin, for example 2-butene or isobutene. Preferably, the olefin is a mono-α-olefin, for example 1-butene or propylene. The most preferred olefin is ethylene. Suitably, mixtures of olefins may be used.

The quantity of olefin present in the feed may be selected within a wide range. Typically, the quantity of olefin present in the feed will be at most 80 mole-%, relative to the total feed. Preferably, it will be in the range of from 0.5 to 70 mole-%, in particular from 1 to 60 mole-%, on the same basis. As used herein, the feed is considered to be the composition which is contacted with the catalyst.

The present epoxidation process may be air-based or oxygen-based, see "Kirk-Othmer Encyclopedia of Chemical Technology", $3^{rd}$ edition, Volume 9, 1980, pp. 445-447. In the air-based process, air or air enriched with oxygen is employed as the source of the oxidizing agent while in the oxygen-based processes high-purity (at least 95 mole-%) or very high purity (at least 99.5 mole-%) oxygen is employed as the source of the oxidizing agent. Reference may be made to U.S. Pat. No. 6,040,467, incorporated by reference, for further description of oxygen-based processes. Presently most epoxidation plants are oxygen-based and this is a preferred embodiment of the present invention.

The quantity of oxygen present in the feed may be selected within a wide range. However, in practice, oxygen is generally applied in a quantity which avoids the flammable regime. Typically, the quantity of oxygen applied will be within the range of from 1 to 15 mole-%, more typically from 2 to 12 mole-% of the total feed.

In order to remain outside the flammable regime, the quantity of oxygen present in the feed may be lowered as the quantity of the olefin is increased. The actual safe operating ranges depend, along with the feed composition, also on the reaction conditions such as the reaction temperature and the pressure.

A reaction modifier may be present in the feed for increasing the selectively, suppressing the undesirable oxidation of olefin or olefin oxide to carbon dioxide and water, relative to the desired formation of olefin oxide. Many organic compounds, especially organic halides and organic nitrogen compounds, may be employed as the reaction modifiers. Nitrogen oxides, organic nitro compounds such as nitromethane, nitroethane, and nitropropane, hydrazine, hydroxylamine or ammonia may be employed as well. It is frequently considered that under the operating conditions of olefin epoxidation the nitrogen-containing reaction modifiers are precursors of nitrates or nitrites, i.e. they are so-called nitrate- or nitrite-forming compounds. Reference may be made to EP-A-3642 and U.S. Pat. No. 4,822,900, which are incorporated herein by reference, for further description of nitrogen-containing reaction modifiers.

Organic halides are the preferred reaction modifiers, in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred reaction modifiers are ethyl chloride, vinyl chloride and ethylene dichloride.

Suitable nitrogen oxides are of the general formula $NO_x$ wherein x is in the range of from 1 to 2, and include for example NO, $N_2O_3$ and $N_2O_4$. Suitable organic nitrogen compounds are nitro compounds, nitroso compounds, amines, nitrates and nitrites, for example nitromethane, 1-nitropropane or 2-nitropropane. In preferred embodiments, nitrate- or nitrite-forming compounds, e.g. nitrogen oxides and/or organic nitrogen compounds, are used together with an organic halide, in particular an organic chloride.

The reaction modifiers are generally effective when used in small quantities in the feed, for example up to 0.1 mole-%, relative to the total feed, for example from $0.01 \times 10^{-4}$ to 0.01 mole-%. In particular when the olefin is ethylene, it is preferred that the reaction modifier is present in the feed in a quantity of from $0.1 \times 10^{-4}$ to $500 \times 10^{-4}$ mole-%, in particular from $0.2 \times 10^{-4}$ to $200 \times 10^{-4}$ mole-%, relative to the total feed.

In addition to the olefin, oxygen and the reaction modifier, the feed may contain one or more optional components, such as carbon dioxide, inert gases and saturated hydrocarbons. Carbon dioxide is a by-product in the epoxidation process. However, carbon dioxide generally has an adverse effect on the catalyst activity. Typically, a quantity of carbon dioxide in the feed in excess of 25 mole-%, preferably in excess of 10 mole-%, relative to the total feed, is avoided. A quantity of carbon dioxide of less than 3 mole-%, preferably less than 2 mole-%, in particular in the range of from 0.3 to less than 1 mole-%, relative to the total feed, may be employed. Under commercial operations, a quantity of carbon dioxide of at least 0.1 mole-%, or at least 0.2 mole-%, relative to the total feed, may be present in the feed. Inert gases, for example nitrogen or argon, may be present in the feed in a quantity of from 30 to 90 mole-%, typically from 40 to 80 mole-%. Suitable saturated hydrocarbons are methane and ethane. If saturated hydrocarbons are present, they may be present in a quantity of up to 80 mole-%, relative to the total feed, in particular up to 75 mole-%. Frequently, they are present in a quantity of at least 30 mole-%, more frequently at least 40 mole-%. Saturated hydrocarbons may be added to the feed in order to increase the oxygen flammability limit.

The epoxidation process may be carried out using reaction temperatures selected from a wide range. Preferably the reaction temperature is in the range of from 150 to 325° C., more preferably in the range of from 180 to 300° C.

The epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is a gas phase process involving a packed catalyst bed, the GHSV is in the range of from 1500 to 10000 Nl/(l.h). Preferably, the process is carried out at a work rate in the range of from 0.5 to 10 kmole olefin oxide produced per $m^3$ of catalyst per hour, in particular 0.7 to 8 kmole olefin oxide produced per $m^3$ of catalyst per hour, for example 5 kmole olefin oxide produced per $m^3$ of catalyst per hour. As used herein, the work rate is the amount of the olefin oxide produced per unit volume of catalyst per hour and the selectivity is the molar quantity of the olefin oxide formed relative to the molar quantity of the olefin converted. Suitably, the process is conducted under conditions where the olefin oxide partial pressure in the product mix is in the range of from 5 to 200 kPa, for example 11 kPa, 27 kPa, 56 kPa, 77 kPa, 136 kPa, and 160 kPa. The term "product mix" as used herein is understood to refer to the product recovered from the outlet of an epoxidation reactor.

The olefin oxide produced may be recovered from the product mix by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol, a 1,2-diol ether, a 1,2-carbonate, or an alkanolamine.

Conversion of Olefin Oxide to Other Chemicals

The olefin oxide produced in the epoxidation process may be converted into a 1,2-diol, a 1,2-diol ether, a 1,2-carbonate, or an alkanolamine. As this invention leads to a more attractive process for the production of the olefin oxide, it concurrently leads to a more attractive process which comprises producing the olefin oxide in accordance with the invention and the subsequent use of the obtained olefin oxide in the manufacture of the 1,2-diol, 1,2-diol ether, 1,2-carbonate, and/or alkanolamine.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. The presence of such a large quantity of water may favor the selective formation of 1,2-diol and may function as a sink for the reaction exotherm, helping control the reaction temperature. If the proportion of water is lowered, the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

The conversion into the alkanolamine may comprise, for example, reacting the olefin oxide with ammonia. Anhydrous ammonia is typically used to favor the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The 1,2-carbonates may be used as a diluent, in particular as a solvent. Alkanolamines may be used, for example, in the treating ("sweetening") of natural gas.

Unless specified otherwise, the low-molecular weight organic compounds mentioned herein, for example the olefins, 1,2-diols, 1,2-diol ethers, 1,2-carbonates, alkanolamines, and reaction modifiers, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

Having generally described the invention, a further understanding may be obtained by reference to the following examples, which are provided for purposes of illustration only and are not intended to be limiting unless otherwise specified.

EXAMPLES

Example 1

Preparation of Stock Silver Solution

This example describes the preparation of a stock silver impregnation solution used in preparing Catalyst A in Example 2.

A silver-amine-oxalate stock solution was prepared by the following procedure:

In a 5-liter stainless steel beaker, 415 g of reagent-grade sodium hydroxide were dissolved in 2340 ml de-ionized water, and the temperature was adjusted to 50° C.

In a 4-liter stainless steel beaker, 1699 g high purity "Spectropure" silver nitrate was dissolved in 2100 ml de-ionized water, and the temperature was adjusted to 50° C.

The sodium hydroxide solution was added slowly to the silver nitrate solution, with stirring, while maintaining a solution temperature of 50° C. This mixture was stirred for 15 minutes. The pH of the solution was maintained at above 10 by the addition of sodium hydroxide solution as required.

Water was removed from the precipitate created in the mixing step and the conductivity of the water, which contained sodium and nitrate ions, was measured. An amount of fresh deionized water equal to the amount removed was added back to the silver solution. The solution was stirred for 15 minutes at 40° C. The process was repeated until the conductivity of the water removed was less than 90 μmho/cm. 1500 ml fresh deionized water was then added. 630 g of high-purity oxalic acid dihydrate were added in approximately 100 g increments. The temperature was kept at 40° C. (±5° C.) and the pH of the solution was monitored during the addition of the last 130 grams of oxalic acid dihydrate to ensure that the pH did not drop below 7.8 for an extended period of time.

Water was removed from this mixture to leave a highly concentrated silver-containing slurry. The silver oxalate slurry was cooled to 30° C. 699 g of 92 weight percent ethylenediamine (8% de-ionized water) was added while maintaining a temperature no greater than 30° C. The final solution was used as a stock silver impregnation solution for preparing Catalyst A.

Example 2

Preparation of Catalysts

Catalyst A:
Catalyst A was prepared by the incipient wetness technique and the final composition of Catalyst A comprised the following, calculated on the basis of pore volume impregnation: 17.2% w silver; 2 mmole Re/kg; 0.6 mmole W/kg; 2 mmole S/kg; 19 mmole Li/kg; and 5.6 mmole Cs/kg. These values are relative to the weight of the catalyst.

TABLE I

| Carrier A Properties | |
| --- | --- |
| Surface Area (m$^2$/g) | 0.75 |
| Water Absorption (%) | 47.2 |
| Packing Density (kg/m$^3$) | 838 |
| alpha alumina content (%) | 98.4 |
| Nitric Acid Leachables: (ppmw) | |
| Na | 116 |
| K | 87 |
| Ca | 567 |
| Al | 607 |
| Mg | 81 |
| SiO$_2$ | 1474 |

What is claimed is:

1. A catalyst for the epoxidation of an olefin comprising a carrier and, deposited on the carrier, silver, a rhenium promoter, a first co-promoter, and a second co-promoter; wherein:
  a) the quantity of the rhenium promoter deposited on the carrier is greater than 1 mmole/kg, relative to the weight of the catalyst;
  b) the first co-promoter is selected from sulfur, phosphorus, boron, and mixtures thereof;
  c) the second co-promoter is selected from tungsten, molybdenum, chromium, and mixtures thereof;
  d) the total quantity of the first co-promoter and the second co-promoter deposited on the carrier is at most 5.0 mmole/kg, relative to the weight of the catalyst;
  e) wherein the carrier has a monomodal, bimodal or multimodal pore size distribution, with a pore diameter range of 0.01-200 μm, a specific surface area of 0.03-10 m$^2$/g, a pore volume of 0.2-0.7 cm$^3$/g, wherein the median pore diameter of the carrier is 0.1-100 μm and has a water absorption of 10-80%; and
  f) wherein a fluoride-containing species and a strength-enhancing additive are incorporated into the carrier.

2. The catalyst as claimed in claim 1, wherein the quantity of the rhenium promoter is at least 1.25 mmole/kg, relative to the weight of the catalyst.

3. The catalyst as claimed in claim 2, wherein the quantity of the rhenium promoter is in the range of from 1.25 to 50 mmole/kg, relative to the weight of the catalyst.

4. The catalyst as claimed in claim 1, wherein the fluoride-containing species is ammonium fluoride.

5. The catalyst as claimed in claim 1, wherein the strength-enhancing additive is selected from the group consisting of a zirconium species, a lanthanide Group species, a calcium species, a magnesium species, inorganic glass, and mixtures thereof.

6. The catalyst as claimed in claim 1, wherein the catalyst further comprises a further element selected from nitrogen, fluorine, alkali metals, alkaline earth metals, titanium, hafnium, zirconium, vanadium, thallium, thorium, tantalum, niobium, gallium and germanium and mixtures thereof.

7. The catalyst as claimed in claim 1, wherein the catalyst has a water extractable quantity of potassium in the range of from 1.25 to 10 mmole/kg, relative to the weight of the catalyst.

8. The catalyst as claimed in claim 1, wherein the carrier has a surface area of at least 1 m$^2$/g, and a pore size distribution such that pores with diameters in the range of from 0.2 to 10 μm represent at least 70% of the total pore volume and such pores together provide a pore volume of at least 0.27 ml/g, relative to the weight of the carrier.

9. The catalyst as claimed in claim 1, wherein the carrier has a median pore diameter of more than 0.5 µm, and a pore size distribution wherein at least 80% of the total pore volume is contained in pores with diameters in the range of from 0.1 to 10 µm and at least 80% of the pore volume contained in the pores with diameters in the range of from 0.1 to 10 µm is contained in pores with diameters in the range of from 0.3 to 10 µm.

10. A catalyst for the epoxidation of an olefin comprising a carrier and, deposited on the carrier, silver, a rhenium promoter, a first co-promoter, and a second co-promoter; wherein:
   a) the quantity of the rhenium promoter deposited on the carrier is greater than 1 mmole/kg, relative to the weight of the catalyst;
   b) the first co-promoter is selected from sulfur, phosphorus, boron, and mixtures thereof;
   c) the second co-promoter is selected from tungsten, molybdenum, chromium, and mixtures thereof;
   d) the total quantity of the first co-promoter and the second co-promoter deposited on the carrier is at most 5.0 mmole/kg, relative to the weight of the catalyst;
   e) wherein the carrier has a bimodal or multimodal pore size distribution, with a pore diameter range of 0.01-200 µm, a specific surface area of 0.03-10 $m^2/g$, a pore volume of 0.2-0.7 $cm^3/g$, wherein the median pore diameter of the carrier is 0.1-100 µm and has a water absorption of 10-80%; and
   (f) wherein the carrier has at least two log differential pore volume distribution peaks in a pore diameter range of 0.01-100 µm and at least one the peaks is present in a pore diameter range of 0.01-1.0 µm in the pore size distribution as measured by mercury porosimetry, wherein each peak is a maximum value of the log differential pore volume distribution of 0.2 $cm^3/g$ or larger.

11. A catalyst for the epoxidation of an olefin comprising a carrier and, deposited on the carrier, silver, a rhenium promoter, a first co-promoter, and a second co-promoter; wherein:
   a) the quantity of the rhenium promoter deposited on the carrier is greater than 1 mmole/kg, relative to the weight of the catalyst;
   b) the first co-promoter is selected from sulfur, phosphorus, boron, and mixtures thereof;
   c) the second co-promoter is selected from tungsten, molybdenum, chromium, and mixtures thereof;
   d) the total quantity of the first co-promoter and the second co-promoter deposited on the carrier is at most 5.0 mmole/kg, relative to the weight of the catalyst; and
   e) wherein the carrier has a pore diameter range of 0.01-200 µm, a specific surface area of 0.03-10 $m^2/g$, a pore volume of 0.2-0.7 $cm^3/g$, wherein the median pore diameter of the carrier is 0.1-100 µm and has a water absorption of 10-80%; and
   (f) wherein the carrier has a bimodal pore size distribution, with a first mode of pores which has a mean diameter ranging from about 0.01 m to about 5 µm, and a second mode of pores which has a mean diameter ranging from about 5 µm to about 30 µm.

12. The catalyst as claimed in claim 1, wherein the carrier has a monomodal pore size distribution, a pore volume from pores with less than 1 micron in diameter of less than 0.20 ml/g, a pore volume from pores with greater than 5 micron in diameter of less than 0.20 ml/g, and at least 40 percent of pore volume from pores between 1 micron in diameter and 5 microns in diameter.

13. A process for preparing a catalyst for the epoxidation of an olefin comprising depositing silver, a rhenium promoter, a first co-promoter, and a second co-promoter on a carrier; wherein
   a) the quantity of the rhenium promoter deposited on the carrier is greater than 1 mmole/kg, relative to the weight of the catalyst;
   b) the first co-promoter is selected from sulfur, phosphorus, boron, and mixtures thereof;
   c) the second co-promoter is selected from tungsten, molybdenum, chromium, and mixtures thereof;
   d) the total quantity of the first co-promoter and the second co-promoter deposited on the carrier is at most 5.0 mmole/kg, relative to the weight of the catalyst; and
   e) wherein the carrier has a monomodal, bimodal or multimodal pore size distribution, with a pore diameter range of 0.01-200 µm, a specific surface area of 0.03-10 $m^2/g$, a pore volume of 0.2-0.7 $cm^3/g$, wherein the median pore diameter of the carrier is 0.1-100 µm and has a water absorption of 10-80%; and
   f) wherein a fluoride-containing species and a strength-enhancing additive are incorporated into the carrier.

14. A process for preparing ethylene oxide by reacting a feed comprising ethylene and oxygen in the presence of a catalyst that comprises a carrier and, deposited on the carrier, silver, a rhenium promoter, a first co-promoter, and a second co-promoter; wherein:
   a) the quantity of the rhenium promoter deposited on the carrier is greater than 1 mmole/kg, relative to the weight of the catalyst;
   b) the first co-promoter is selected from sulfur, phosphorus, boron, and mixtures thereof;
   c) the second co-promoter is selected from tungsten, molybdenum, chromium, and mixtures thereof;
   d) the total quantity of the first co-promoter and the second co-promoter deposited on the carrier is at most 5.0 mmole/kg, relative to the weight of the catalyst;
   e) wherein the carrier has a monomodal, bimodal or multimodal pore size distribution, with a pore diameter range of 0.01-200 µm, a specific surface area of 0.03-10 $m^2/g$, a pore volume of 0.2-0.7 $cm^3/g$, wherein the median pore diameter of the carrier is 0.1-100 µm and has a water absorption of 10-80%; and
   f) wherein a fluoride-containing species and a strength-enhancing additive are incorporated into the carrier.

15. A process for preparing a 1,2-diol, a 1,2-diol ether, a 1,2-carbonate, or an alkanolamine comprising:
   preparing ethylene oxide by reacting a feed comprising ethylene and oxygen in the presence of a catalyst that comprises a carrier and, deposited on the carrier, silver, a rhenium promoter, a first co-promoter, and a second co-promoter; wherein:
   a) the quantity of the rhenium promoter deposited on the carrier is greater than 1 mmole/kg, relative to the weight of the catalyst;
   b) the first co-promoter is selected from sulfur, phosphorus, boron, and mixtures thereof;
   c) the second co-promoter is selected from tungsten, molybdenum, chromium, and mixtures thereof;
   d) the total quantity of the first co-promoter and the second co-promoter deposited on the carrier is at most 5.0 mmole/kg, relative to the weight of the catalyst;
   e) wherein the carrier has a monomodal, bimodal or multimodal pore size distribution, with a pore diameter range of 0.01-200 µm, a specific surface area of 0.03-10 $m^2/g$, a pore volume of 0.2-0.7 $cm^3/g$, wherein the median pore diameter of the carrier is 0.1-100 μm and has a water absorption of 10-80%; and f) wherein a fluoride-containing species and a strength-enhancing additive are incorporated into the carrier; and converting the ethylene oxide into the 1,2-diol, the 1,2-diol ether, the 1,2-carbonate, or the alkanolamine.

16. The process as claimed in claim 13, wherein the strength-enhancing additive is selected from the group consisting of a zirconium species, a lanthanide Group species, a calcium species, a magnesium species, inorganic glass, and mixtures thereof.

17. The process as claimed in claim 13, wherein the strength-enhancing additive is selected from the group consisting of a zirconium species, a lanthanide Group species, a calcium species, a magnesium species, inorganic glass, and mixtures thereof.

18. The process as claimed in claim 15, wherein the strength-enhancing additive is selected from the group consisting of a zirconium species, a lanthanide Group species, a calcium species, a magnesium species, inorganic glass, and mixtures thereof.

\* \* \* \* \*